(12) United States Patent
Axelsson et al.

(10) Patent No.: US 11,590,269 B2
(45) Date of Patent: *Feb. 28, 2023

(54) APPARATUS FOR PERFORMING PERITONEAL ULTRAFILTRATION

(71) Applicant: TRIOMED AB, Lund (SE)

(72) Inventors: Mikael Axelsson, Furulund (SE); Stefan Landholm, Malmö (SE); Eva Persson, Veberöd (SE); Hans Bengtsson, Eslöv (SE)

(73) Assignee: TRIOMED AB, Lund (SE)

( * ) Notice: Subject to any disclaimer, the term of this patent is extended or adjusted under 35 U.S.C. 154(b) by 372 days.

This patent is subject to a terminal disclaimer.

(21) Appl. No.: 16/803,691

(22) Filed: Feb. 27, 2020

(65) Prior Publication Data

US 2020/0188570 A1 Jun. 18, 2020

Related U.S. Application Data

(62) Division of application No. 15/528,434, filed as application No. PCT/SE2015/000068 on Nov. 20, 2015, now Pat. No. 10,576,195.

(30) Foreign Application Priority Data

Nov. 21, 2014 (SE) .................................. 1430162-6

(51) Int. Cl.
*A61M 1/28* (2006.01)
*B01D 61/24* (2006.01)

(52) U.S. Cl.
CPC .............. *A61M 1/288* (2014.02); *A61M 1/28* (2013.01); *A61M 1/281* (2014.02); *A61M 1/282* (2014.02);

(Continued)

(58) Field of Classification Search
CPC ........ A61M 1/288; A61M 1/28; A61M 1/281; A61M 1/282; A61M 1/287;

(Continued)

(56) References Cited

U.S. PATENT DOCUMENTS 4,618,343 A 10/1986 Polaschegg
4,687,580 A * 8/1987 Malbrancq .......... A61M 1/3604
210/651

(Continued)

FOREIGN PATENT DOCUMENTS

GB 1462349 1/1977
JP H07-0275358 A 10/1995

(Continued)

*Primary Examiner* — Joseph W Drodge
(74) *Attorney, Agent, or Firm* — Birch, Stewart, Kolasch & Birch, LLP

(57) ABSTRACT

An apparatus for ultrafiltration of a patient being overhydrated due to congestive heart failure, comprising a tube set including a connector (21) for connection to a patient line (3) for access to the peritoneal cavity of the patient. A flow pump (41-43) is arranged for addition and removal outflow and inflow (recirculation) of fluid from/to the peritoneal cavity. An osmotic agent peristaltic pump (16) is arranged for replenishment of glucose solution to the fluid added to the peritoneal cavity for promoting ultrafiltration. The glucose is replenished intermittently for keeping a concentration of glucose substantially constant in the peritoneal cavity. The flow pump comprises a pressure chamber (43) with rigid walls and a flexible pump bag (41) arranged therein. An air pump (45) pressurizes the chamber for outflow of fluid from the peritoneal cavity by a sub pressure and inflow of fluid to the peritoneal cavity by an overpressure, which pressures are maintained within safe limits.

15 Claims, 10 Drawing Sheets

(52) U.S. Cl.
CPC ........... *A61M 1/287* (2013.01); *B01D 61/243* (2013.01); *A61M 2205/12* (2013.01); *A61M 2205/3331* (2013.01); *A61M 2205/3334* (2013.01)

(58) Field of Classification Search
CPC ...... A61M 2205/12; A61M 2205/3331; A61M 2205/3334; A61M 2205/07; A61M 2205/8206; A61M 1/1656; A61M 1/1678; A61M 1/284; B01D 61/24; B01D 61/243; B01D 61/30
See application file for complete search history.

(56) References Cited

U.S. PATENT DOCUMENTS

| | | | |
|---|---|---|---|
| 5,004,459 | A | 4/1991 | Peabody et al. |
| 5,141,493 | A | 8/1992 | Jacobsen et al. |
| 5,722,947 | A | 3/1998 | Jeppsson et al. |
| 5,944,684 | A | 8/1999 | Roberts et al. |
| 6,409,699 | B1 | 6/2002 | Ash |
| 6,585,682 | B1 * | 7/2003 | Haraldsson ............. A61M 1/28 604/28 |
| 6,818,179 | B1 * | 11/2004 | Edgson ..................... A61L 2/04 422/38 |
| 6,967,002 | B1 * | 11/2005 | Edgson ................. A61L 2/0023 422/38 |
| 10,576,195 | B2 * | 3/2020 | Axelsson ............. A61M 1/288 |
| 10,709,831 | B2 * | 7/2020 | Wallenås ................ A61M 1/28 |
| 10,946,130 | B2 * | 3/2021 | Bengtsson ............. A61M 1/287 |
| 2004/0019312 | A1 | 1/2004 | Childers et al. |
| 2004/0215129 | A1 * | 10/2004 | Edgson ..................... A61L 2/04 604/29 |
| 2007/0179431 | A1 | 8/2007 | Roberts et al. |
| 2008/0051696 | A1 | 2/2008 | Curtin et al. |
| 2010/0069817 | A1 * | 3/2010 | Falkvall ............... A61M 1/1668 604/416 |
| 2010/0191181 | A1 * | 7/2010 | Childers ............... A61M 1/281 604/29 |
| 2010/0312174 | A1 | 12/2010 | Hoffman |
| 2012/0029325 | A1 | 2/2012 | Neftel |
| 2013/0006171 | A1 | 1/2013 | Griessmann et al. |
| 2014/0018727 | A1 | 1/2014 | Burbank et al. |
| 2014/0158538 | A1 | 6/2014 | Collier et al. |
| 2014/0276373 | A1 * | 9/2014 | Minkus .................. A61M 1/282 604/28 |
| 2014/0316332 | A1 * | 10/2014 | Lo .......................... A61M 39/24 604/28 |
| 2020/0030517 | A1 * | 1/2020 | Basati ................ A61B 5/14507 |

FOREIGN PATENT DOCUMENTS

| | | |
|---|---|---|
| JP | 2001-190662 A | 7/2001 |
| WO | WO 95/35124 A1 | 12/1995 |
| WO | WO 99/06082 A1 | 2/1999 |
| WO | WO 01/58509 A1 | 8/2001 |
| WO | WO 03/063929 A1 | 8/2003 |
| WO | WO 03/099353 A2 | 12/2003 |
| WO | WO 2012/129501 A2 | 9/2012 |
| WO | WO 2013/070172 A1 | 5/2013 |
| WO | WO 2013/109922 A1 | 7/2013 |
| WO | WO 2015/130205 A1 | 9/2015 |

* cited by examiner

APPARATUS FOR PERFORMING PERITONEAL ULTRAFILTRATION

CROSS-REFERENCE TO RELATED APPLICATIONS

This application is a Divisional of copending U.S. application Ser. No. 15/528,434, filed May 19, 2017 which is the National Phase under 35 U.S.C. § 371 of International Application No. PCT/SE2015/000068 filed Nov. 20, 2015, which claims the benefit under 35 U.S.C. § 119(a) to Patent Application No. 1430162-6, filed in Sweden on Nov. 21, 2014, all of which are hereby expressly incorporated by reference into the present application.

FIELD OF INVENTION

The present invention relates to an apparatus for performing peritoneal ultrafiltration of a patient in need thereof, for example due to congestive heart failure.

BACKGROUND

Diuretic-resistant congestive heart failure is a problem of growing significance. It is related closely to the cardio-renal syndrome, which is characterized by chronic abnormalities in cardiac function, causing impaired renal function and progressive chronic kidney disease.

Congestive Heart Failure patients can benefit from fluid removal by ultrafiltration. These patients normally have functional kidneys, but suffer from fluid overload. The kidneys of these patients are generally healthy but are not fully functioning due to the failing heart with increased venous blood pressure and sometimes low arterial blood pressure. Because the kidneys are not fully functioning, fluid builds up in the patient and the fluid overload contributes to stress on the already partly failing heart.

The proper control of sodium and water balance is of vital importance because up to 80% of hospitalizations from Congestive Heart Failure are due to acute over-hydration and only 5% are due to low cardiac output.

The patent document U.S. Pat. No. 7,135,008B2 discloses a method and apparatus for the extracorporeal treatment of blood by utilizing a dual lumen catheter assembly peripherally inserted in the blood vessels for the continuous removal and return of blood for renal replacement treatment, in particularly, treatment of congestive heart failure and fluid overload by ultrafiltration. A catheter is inserted in a peripheral vein and maneuvered upward through the vascular system to access the reservoir of blood in the large or great veins for continuous blood withdrawal and treatment. Airtight connectors are incorporated in the catheter assembly to overcome the untoward effects of negative pressure in blood withdrawal.

However, ultrafiltration via extracorporeal treatment of blood, results in risks associated with access to the vascular system. In addition, the ultrafiltration may be excessive resulting in hypotension.

A promising ultrafiltration method which do not use extracorporeal blood treatment is used in peritoneal dialysis, in which the endogenous peritoneal membrane is used for ultrafiltration. A peritoneal ultrafiltration fluid is installed in the peritoneal cavity. The fluid comprises an osmotic agent, such as glucose or Icodextrin or others, causing ultrafiltration. Peritoneal ultrafiltration is more gentle to the patient and seldom results in hypotension. In addition, peritoneal ultrafiltration may be used daily outside the hospital without or with limited need for medically trained professionals.

With the present PD regiments, the glucose based fluid must be replaced every four hours and has optimal ultrafiltration for only 2 to 3 hours. Each replacement takes about one hour and increases the risk of infection. The frequent replacements also reduce the freedom and quality of life for the patients.

In addition, the use of glucose may result in the absorption of glucose into the circulation, which may lead to hyperglycemia, hyperinsulinemia, and obesity. Icodextrin may cause other problems.

Addition of an osmotic agent to the peritoneal cavity may be detrimental to the peritoneal membrane if the concentration of the osmotic agent is excessive. Thus, the peritoneal membrane needs to be protected from local high concentration of osmotic agent, such as glucose, in the introductory place of the peritoneal cavity.

Thus, there is a need for a method of producing a peritoneal dialysis fluid, which is optimized with regard to peritoneal ultrafiltration of patients with heart failure. In addition, there is a need for an apparatus for performing peritoneal ultrafiltration.

SUMMARY OF THE INVENTION

Accordingly, an object of the present invention is to mitigate, alleviate or eliminate one or more of the above-identified deficiencies and disadvantages singly or in any combination.

In an aspect, there is provided an apparatus for ultrafiltration of a patient in need thereof, for example a patient being overhydrated due to congestive heart failure, comprising a patient tube comprising a connector for connection to a patient line for access to a peritoneal cavity of the patient; a flow pump for removal of a fluid via said patient tube in an outflow from the peritoneal cavity and to a pump bag and for introduction of the fluid in an inflow from the pump bag to the peritoneal cavity; a glucose bag, comprising concentrated glucose solution; a glucose pump for addition of concentrated glucose from said glucose bag into at least one of said outflow and inflow of fluid by said flow pump; whereby the glucose is diluted and replenished intermittently for keeping a concentration of the osmotic agent substantially constant in the peritoneal cavity.

In an embodiment, the flow pump may comprise: a pressure chamber having rigid walls, wherein said pump bag is arranged inside said pressure chamber, an air pump for generating a negative pressure inside said pressure chamber for removal of fluid in said outflow from said peritoneal cavity into said pump bag, and for generating a positive pressure for introduction of fluid in said inflow from said pump bag to the peritoneal cavity.

The glucose bag may comprise glucose at a concentration of about 10%, 15%, 20%, 25%, 35% or 40% or 50%, and wherein the glucose is diluted to a final concentration of less than 3% before addition to the peritoneal cavity.

The apparatus may further comprise a flow meter for measuring the flow rate of said inflow or outflow fluid. The apparatus may further comprise a cassette in which the flow of glucose from the glucose bag is diluted by said inflow and/or said outflow of fluid. The apparatus may further comprise a fluid pressure meter connected to the cassette for sensing the pressure during said inflow and/or said outflow and for emitting an alarm if the pressure exceeds a first predetermined level. The fluid pressure meter may be arranged to measure the pressure in the cassette before said inflow to the peritoneal cavity as an indication of the pressure in the peritoneal cavity and to emit an alarm if the pressure is above a second predetermined pressure.

In a further embodiment, an air pressure meter may be arranged in said pressure chamber and may be arranged to compare the pressure inside said pressure chamber with the pressure in said cassette for indicating a flow when the pressure difference is smaller than a third predetermined value.

In a still further embodiment, the air pressure meter in said pressure chamber may be arranged to indicate when the pump bag is filled by: measuring a decrease of pressure chamber pressure to an outflow pressure; measuring a constant pressure chamber pressure during said outflow; measuring a decrease of pressure chamber pressure to a minimum pressure after said outflow; wherein an evaluation device is arranged to indicate an error if a time period of constant outflow chamber pressure is less than a predetermined time period, for example less than 2 minutes.

In a yet further embodiment, the air pressure meter in said pressure chamber may be arranged to indicate when the pump bag is empty by: measuring an increase of pressure chamber pressure to an inflow pressure; measuring a constant pressure chamber pressure during said inflow; measuring an increase of pressure chamber pressure to a maximum pressure after said inflow; wherein an evaluation device is arranged to indicate an error if a time period of constant chamber inflow pressure is less than a predetermined time period, for example less than 2 minutes.

BRIEF DESCRIPTION OF THE DRAWINGS

Further objects, features and advantages of the invention will become apparent from the following detailed description of embodiments of the invention with reference to the drawings, in which.

DETAILED DESCRIPTION OF EMBODIMENTS

Below, several embodiments of the invention will be described. These embodiments are described in illustrating purpose in order to enable a skilled person to carry out the invention and to disclose the best mode. However, such embodiments do not limit the scope of the invention. Moreover, certain combinations of features are shown and discussed. However, other combinations of the different features are possible within the scope of the invention.

Figure 1:
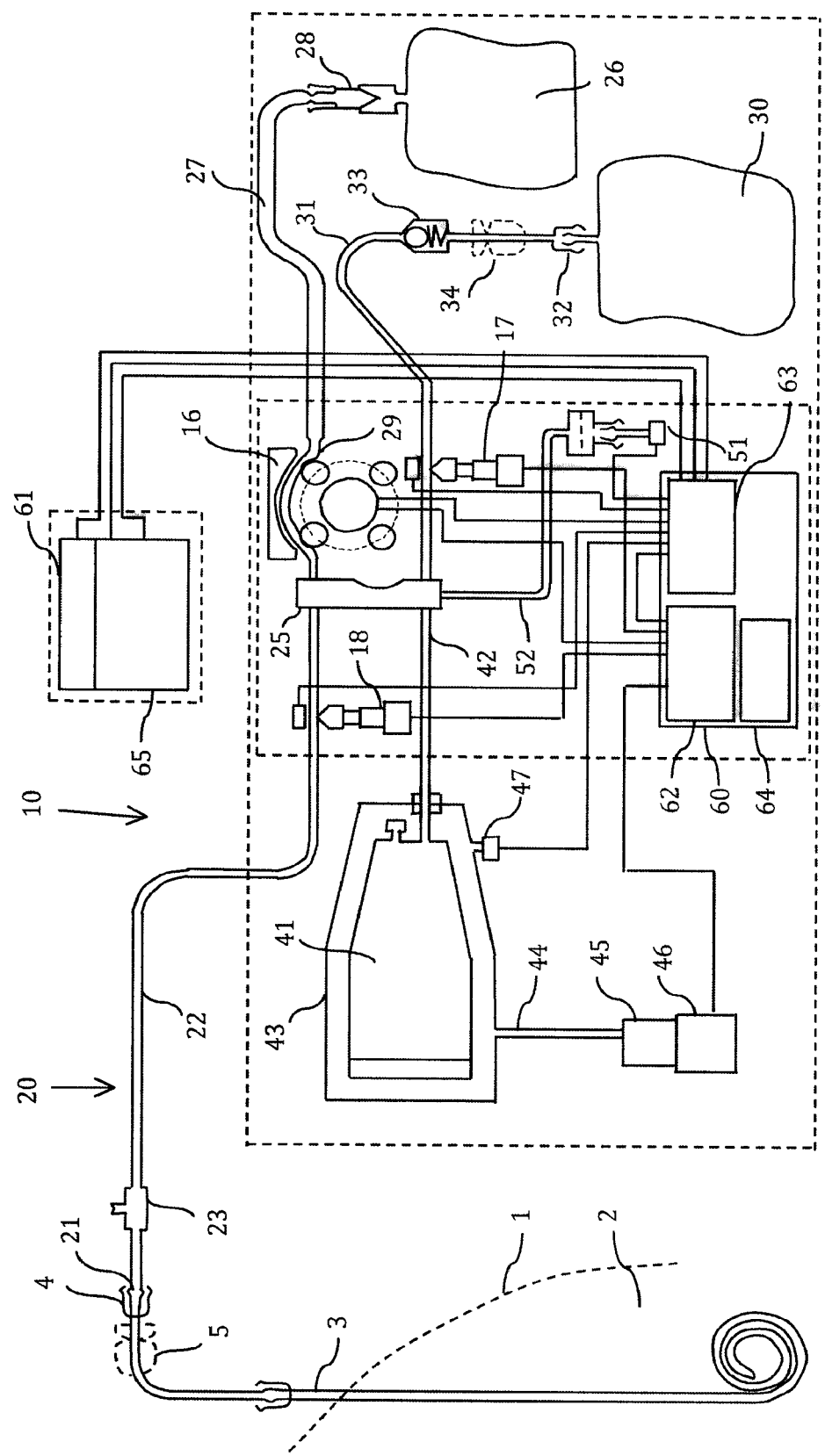
FIG. 1 is a schematic diagram of a first embodiment of an apparatus for providing and regenerating an ultrafiltration fluid to a patient.

FIG. 1 discloses a patient 1, which is provided with a patient line 3, which may be a conventional patient line connected to a conventional peritoneal catheter installed in the peritoneal cavity of the patient. The patient line 3 connects the patient's peritoneal cavity 2 with the surrounding environment. The provision of the patient line is a standard procedure and is made at a hospital. After a few days, the patient line may be used for inflow and outflow of a peritoneal fluid in the peritoneal cavity. The peritoneal fluid is in contact with a peritoneal membrane comprising capillary blood vessels. The peritoneal membrane will exchange ions and substances between the blood and the peritoneal fluid. Peritoneal dialysis has been performed routinely for several decades and was used already during the 1940's.

The patient line 3 ends with a connector 4 of standard type, for example a Luer connector. A patient line clamp 5 is arranged on the patient line 3 adjacent the connector 4 for closing and opening of the patient line.

An apparatus 10 according to a first embodiment of the invention comprises a tube set 20, a glucose pump 16, a drain valve 17 and a patient valve 18. The pump 16 is shown as peristaltic pump of a type commonly used in a dialysis apparatus. However, other types of pumps may be used. The valves are electrically operated valves and act upon a tube for occlusion of the tube. However, any type of valve may be used.

The tube set comprises an end connector 21, which mates with the connector 4 of the patient line 3. The end connector 21 is arranged at a distal end of a patient tube 22, which in addition comprises a port 23 adjacent the end connector 21. The port 23 may be used for sampling the fluid in the patient line. A proximal end of the patient tube 22 is connected to a cassette 25 via the patient valve 18. Thus, the interior of the cassette 25 is connected to the end connector 21.

The tube set further comprises a glucose bag 26, which is connected to the cassette 25 via a glucose tube 27. The glucose tube 27 is connected to a pump segment 29 passing through the glucose pump 16 and further to the cassette 25. A connector or spike 28 is arranged at the end of the glucose tube 27 for being inserted in the glucose bag 26 for establishing fluid communication between the glucose bag 26 and the glucose tube 27. The glucose bag 26 is, thus, connected to the cassette 25, via pump 16. The glucose bag 27 may alternatively be integrated in the tube set before sterilization of the entire tube set, thereby removing a cause of probable microorganism entry at connection of the glucose bag.

The tube set further comprises a drain bag 30, which is connected to a drain tube 31 via a connector 32, which may be a Luer connector. The drain tube 31 is connected to the cassette 25. The drain valve 17 acts upon the drain tube 31 for occluding the drain tube when activated. Thus, the drain bag 30 is connected to the cassette 25. The drain tube 31 comprises a back-flow valve 33, which allows flow from the cassette 25 to the drain bag 30 but prevents flow in the opposite direction. A drain bag clamp 34 is arranged for closing the drain line. Since there is never any flow from the drain bag to the cassette 25, there is no risk for entry of microorganisms in this route. Thus, the drain bag can be connected and disconnected at will. A sensor (not shown) may be arranged for indicating that a drain bag is connected. The system may be arranged to use this sensor for preventing opening of valve 17 unless a drain bag is connected.

The tube set further comprises a pump bag 41 connected to a pump tube 42. The pump tube 42 is connected to the cassette 25. Thus, the pump bag 41 is connected to the cassette 25. The pump bag 41 may have a volume of for example 160 ml. The pump bag 41 is arranged in a closed chamber 43 having rigid walls and a constant inner volume, as described in further detail below. The closed chamber 43 is, via an air tube 44, connected to an air pump 45, which is operated by an electric motor 46. When the motor is driven in a forward direction, air is pumped into chamber 43 and when the motor is driven in a backward direction, air is pumped out of chamber 43.

The pump 45 is able to produce a maximum overpressure or positive pressure, which may be for example about +0.2 Bar and a minimum subpressure or negative pressure, which may be for example about −0.2 Bar in relation to ambient pressure. The pressure inside the pump bag 41 is, consequently, always between about +0.2 Bar and about −0.2 Bar.

Thus, when the air pump 45 delivers an overpressure, pump bag 41 is exposed to an external overpressure of maximum +0.2 Bar, which results in that fluid inside pump bag 41 is expelled out of pump bag 41 to the cassette 25. When, the air pump 45 delivers a subpressure, pump bag 41 is exposed to an external subpressure of minimum −0.2 Bar (between 0 Bar and −0.2 Bar), which results in that fluid inside pump bag 41 is sucked into pump bag 41 from the cassette 25. Thus, pump bag 41 operates as a fluid pump having controlled and restricted maximum and minimum pressures, as described in further detail below.

The cassette 25 is, in addition, connected to a fluid pressure meter 51 via a pressure meter tube 52. A chamber air pressure meter 47 is arranged in the rigid wall of the chamber 43. The operation of the apparatus is controlled by a computer 60, which is operated by a remote control 61.

The tube set may be PVC tubes of a medical grade. The pump segment 29 may be made of a silicon material. The peristaltic pump may also operate as a flow meter, since a specific volume of fluid is normally pumped per revolution of the pump. Thus, the peristaltic pump has a revolution meter or sensor 49 (see FIG. 2), which measures the rotational position of the peristaltic pump 16.

The apparatus 10 according to the first embodiment may be operated in the following manner.

When the apparatus 10 is to be initiated, for example in the morning, the patient first installs a start ultrafiltration fluid into the peritoneal cavity. The start ultrafiltration fluid may be a conventional fluid used for peritoneal dialysis or a specially composed ultrafiltration fluid having a slightly different composition, for example excluding glucose, which makes sterilization of the ultrafiltration fluid more easy. Examples of compositions of the start fluid are given below.

The installation of the fluid may take place in any suitable way, for example by connecting a CAPD fluid set to the patient connector 4 (which is not connected to the apparatus). The CAPD fluid set (not shown) may be a conventional PD medicinal product comprising a fluid bag connected by a tube to a drain bag. The tube is provided with a T-connector for connection to the patient connector 4. The CAPD fluid set is operated by first connecting the T-connector to the patient connector 4 in an aseptic manner and arranging the fluid bag at a stand about 50 cm above the patient connector 4 and the drain bag at floor level. By operating tube clamps, a small volume of fluid is allowed to flow from the fluid bag to the drain bag in order to rinse the tube set. Then, the fluid from fluid bag is allowed to flow into the patients peritoneal cavity via the patient connector 4 by gravity force until a sufficient volume of fluid has been installed in the patient peritoneal cavity. The installed CAPD fluid may be preheated to a temperature close to the body temperature. Finally, the T-connector is disconnected from the patient connector 4 and the patient connector 4 is connected to the end connector 21 of the apparatus 10.

The tube set 20 of apparatus 10 is initially empty of liquid and partly filled with air.

When the apparatus 10 is connected to the patient connector 4 via end connector 21, the tube set 20 should be initiated or primed in order to remove the air and to remove micro organism from the device. During sterilization and storage, the inner surfaces of the plastic tubes may comprise small quantities of toxic products, and it is generally also beneficial to remove such possible products.

Thus, the tube set is first primed in the following manner by using the fluid already installed in the peritoneal cavity of the patient. In a first step, patient valve 18 is closed and drain valve 17 is opened. The glucose pump 16 is operated in order to move any air out of glucose tube 27 and pump glucose solution into cassette 25 for displacing air from cassette 25 to drain bag. In addition, air pump 45 is operated (simultaneously or in advance) by motor 46 for generating an overpressure in the chamber 41, thereby displacing air out of pump bag 41 to drain bag. When the cassette and the tubes are substantially filled with glucose solution, the glucose pump is stopped and drain valve 17 and patient valve 18 are closed. In a second step, the drain valve 17 is kept closed and the patient valve 18 is opened and air pump motor 46 is reversed for generating a sub pressure in the pressure chamber 43 and pump bag 41, whereby fluid is sucked from the patient peritoneal cavity and into pump bag 41 until the pump bag 41 is (at least partly) filled. In this step, any air in the interior of the patient tube 20 is removed to the pump bag. In addition, microorganisms that may have been introduced into the line set during the connection of the line set to patient line may be removed the same way. In a third step, patient valve 18 is closed and drain valve 17 is opened, and the air pump motor is operated in its forward direction for generating an overpressure in the chamber 43. Thus, fluid and air inside pressure chamber 41 is expelled into the drain bag. In a fourth step, both drain valve 17 and patient valve 18 are closed while air pump 45 still generates maximum air pressure (about +0.2 Bar) and glucose pump is operated to pump a small amount of fluid into cassette 25. The fluid pressure meter 51 and the air pressure meter 47 are read in order to verify that they both indicates the same pressure of about +0.2 Bar. This is a test that the system and valves does not include any leakage. Then, the patient valve 18 is opened and the airpump is stopped, whereby the pressure inside the cassette becomes normal, about the atmosphere pressure, which indicates that the patient line 22 does not include any kinks and that fluid transfer to the peritoneal cavity can take place unimpeded. Additionally, the glucose pump may be reversed, with the patient valve 18 and the drain valve 17 closed, in order to remove a small amount of fluid from the cassette, thereby generating a negative pressure in the cassette, which is sensed by the fluid pressure meter 51. Alternatively the air pump can be used for generating a negative pressure. This measure is done for ensuring there is no leakage in the system.

In addition, the fluid pressure meter 51 can be calibrated in order to compensate for any height difference between the peritoneal cavity and the apparatus, and also for any overpressure inside the peritoneal cavity. Now, the priming sequence is finished.

There are alternative priming steps as indicated below, and the steps can be performed in another sequence. Some of the steps may be excluded, for example the step of testing that the system and valves does not include any leakage and/or the step of testing that the patient line does not include any kinks and that fluid transfer to and from the peritoneal cavity can take place unimpeded.

If the initially installed fluid does not include any glucose, it is desired, immediately after priming, to install glucose into the peritoneal cavity in order to start treatment.

A treatment cycle may be performed in the following manner.

Firstly, the patient valve 18 is opened. The drain valve 17 is always closed during cycling. The air pump motor 46 is operated in the backward direction in order to generate a subpressure in the pump bag 41, whereby fluid from the patient peritoneal cavity in a removal step is transferred to the pump bag 41 until the pump bag 41 is full, which corresponds to about 160 ml. Then, the air pump motor 46 is operated in the forward direction in order to generate an overpressure in the pump bag 41, whereby the fluid is displaced from the pump bag 41 back to the patient in a fill step. During the fill step, the glucose pump 16 is operated in order to pump glucose fluid from glucose bag 26 to the cassette 25 and further to the patient. By this operation, the concentrated glucose solution delivered by the glucose pump 16 is diluted on-line in the cassette in order not to harm the peritoneal cavity membranes when introduced.

Generally, it is believed that a glucose concentration of less than 3% is well tolerated. If the glucose in glucose bag 26 has a concentration of 10%, a dilution of at least 7:3 is required. Since the concentration of glucose in the fluid removed from the peritoneal cavity may vary, for example dependent on the glucose concentration in the initial fill, it is contemplated to include a large safety margin, of for example 9:1 (or 19:1), i.e. 1 ml/min of glucose solution (10%) is added to 9 ml/min (19 ml/min) of fluid from pump bag 41. Thus, for each cycle of about 160 ml, there is added a maximum of 16 ml (8 ml) of glucose (10%) which is equivalent to 1.6 g (0.8 g) glucose. If it is required to replenish a maximum of 4 g glucose per hour, a cycle needs to be performed each 25 minutes. If a cycle is performed 4 times per hour, a smaller amount of glucose is added each time. This may be done by reducing the addition rate of glucose or by decreasing the time during which the glucose pump is operated.

The concentrated glucose solution is diluted on-line, which means that the concentrated glucose solution is added to a larger flow of fluid from pump bag 41 in cassette 25 and mixed with said larger flow during inflow to the patient. The two flows are initially mixed in the cassette 25 and further mixed during the flow in the patient tube 22 so that the fluid exiting the patient tube 22 is substantially mixed.

Another alternative is to add the concentrated glucose solution to the outflow from the peritoneal cavity to the pump bag 41, wherein the glucose is added i the cassette 25. In this manner, the glucose is diluted and mixed in the pump bag 41 before being reintroduced to the patient.

A further alternative is to combine the two methods and add concentrate glucose solution to both the outflow from the peritoneal cavity and to the inflow to the peritoneal cavity.

A still further alternative is to add a metered amount of concentrated glucose solution to the pump bag before initiation of a cycle, whereupon fluid is removed from the peritoneal cavity into pump bag in an outflow, in order to mix with the glucose already present in the pump chamber.

The object is to add a predetermined amount of glucose during a fill cycle. However, the amount of fluid from pump bag 41 is of less importance as long as the amount is sufficiently large for diluting the concentrated glucose solution to below 3%. Thus, it is important to ensure that the pump bag 41 comprises a sufficient amount of fluid before the fill phase, see further below.

It is desired to keep the concentration of glucose in the peritoneal cavity as low as possible for the required ultrafiltration. Thus, the glucose flow pump is operated with a low and constant flow speed during each cycle.

A sufficient amount of glucose is introduced during each cycle, which is calculated or estimated in advance based on the absorption of glucose by the patient. The speed of the glucose pump is adjusted so that the concentration of glucose in the fluid administered to the patient is always lower than a predetermined safe concentration, for example lower than 3%. The time duration during which the glucose pump is operated is adjusted by the cycler, so that the glucose absorbed by the peritoneal membrane is replenished. If the cycling is performed four times per hour, about 10 ml glucose of 10% may be diluted and added during each cycle period. If glucose of a concentration of 20% is used, only 5 ml is added per cycle, etc. The amount is adjusted in dependence of the selected regimen, Low, Medium or High glucose concentration. In addition, the amount may be adjusted by the physician according to the patient needs. The predetermined safe concentration may alternatively be 2%, 2.5%, 3%, 3.5%, 4%, 4.5%, 5%, 6%, 7%, 8%, 9% or 10%.

If there is no glucose installed during the start fill, the first few, for example three, cycles should include a sufficient amount of glucose for increasing the glucose concentration to the desired concentration. The following cycles add sufficient amounts of glucose for keeping the desired concentration. If the glucose concentration in glucose bag 26 is about 10% and a treatment concentration of 1% is required, about 15 g of glucose, which corresponds to 150 ml of glucose solution at 10% should be added in the initial fills, if it is estimated that the patient has about 1.5 liter of fluid inside the peritoneal cavity. It may take approximately three cycles until the glucose concentration has been increased to the required concentration. It is believed that a gentle increase of the glucose concentration during for example 30 minutes in for example three consecutive cycles of 10 minutes may be beneficial for the peritoneal membrane.

If the start fill comprises glucose, there is no need for an initial glucose fill cycle (or several).

Alternatively, the start fill may comprise a small amount of glucose, for example 0.5% or 0.75%, which is increased during the following cycles to the required concentration.

The apparatus may include three levels of glucose administration rates, to be set at the start of the treatment, such as Low, Medium and High administration rates. Low may be for example addition of 2 g of glucose per hour, Medium may be for example 3 g/h and High may be for example 4 g/h.

During the treatment, liquid is removed from the patient liquid body volume (as desired) and is accumulated inside the peritoneal cavity, which may result in an increase of the intraperitoneal pressure, which is counterproductive. In addition, the addition of glucose increases the fluid volume inside the peritoneal cavity, especially if glucose solution at low concentration (10%) is used. Thus, it is desired to remove surplus fluid. This is done in a drain cycle.

During the drain cycle, fluid is sucked into pump bag 41 as described above. Then, the patient valve 18 is closed and the drain valve 17 is opened (provided that a drain bag sensor, if present, indicates that a drain bag is connected). Upon pressurizing the pressure chamber 43 by pump 45, the fluid inside pump bag 41 is expelled to the drain bag 30. The volume drained is about 160 ml per drain cycle. It may be appropriate to make one drain each hour. However, if the patient feels that the peritoneal cavity pressure is too high, more drain cycles may be performed. Too many drain cycles per hour, may be prevented by the system or apparatus.

When the fluid including glucose has been installed in the peritoneal cavity, exchange of substances takes place between the installed fluid and the blood. In particular, glucose is slowly absorbed by the blood, since the concentration of glucose in the fluid is larger than the glucose concentration in blood. However, since the absorption of glucose is slow, water will be transported in the other direction through the walls of the capillaries into the peritoneal cavity, due to osmotic pressure of the glucose solution, in order to dilute the installed fluid. As long as the concentration of glucose in the installed fluid is larger than in blood, such water transport takes place. Such water transport is equivalent to ultrafiltration. Since the blood will lose some water, this water will be replaced from other portions of the body, resulting in removal of surplus water from the body tissue.

The glucose, which has been absorbed by the blood, needs to be replaced in the peritoneal cavity in order to maintain the glucose gradient and ultrafiltration. The principle used in the embodiments is that an intermittent replacement of glucose is performed in order to achieve a substantially constant ultrafiltration, which is believed to alleviate symptoms.

The dosage of glucose may be determined in advance and adjusted according to a prescription by a doctor. The patient may also adjust the replenishment of glucose, at least within some limits. For example, if the patient feels pain, this may be due to a too high glucose concentration, especially if the glucose solution has a low pH, and the patient may decrease such concentration by pressing a button. Pressing the button may result in reduction of glucose replenishment during the next few cycles or during the rest of the treatment.

In an alternative embodiment, a pressure meter may suggest initiation of a drain cycle if the pressure inside the peritoneal cavity increases above a predetermine threshold. The fluid pressure meter 51 continuously senses the pressure in the cassette 25. At the start of a cycle, the first action is to open the patient valve 25, whereby the fluid pressure meter 51 measures the start pressure present inside the peritoneal cavity, plus/minus the height difference of the fluid pressure meter 51 in relation to the peritoneal cavity (before initiation of pump 45). If the start pressure is above a predetermined pressure level, an indication may be given to the user, that a drain cycle may be appropriate. If the drain button is pressed within a predetermined time after initiation of a cycle, for example within 120 seconds, the present cycle is converted to a drain cycle. A drain cycle may also be initiated by the user without a signal from the fluid pressure meter 51.

There is always a risk that too much fluid is drained from the peritoneal cavity. Thus, no more than three drain cycles are allowed per hour. Other limitations can be programmed into the processor program.

The air pump 45 is constructed and/or adjusted so that the flow of air through the pump is relatively small and controlled. The air flow should be sufficiently large for generating a flow of fluid from and to the patient of about 10 to 40 ml/min for example 32 ml/min. Thus, a complete cycle may take about 10 minutes.

It is not necessary to completely fill the pump bag 41 during each cycle. Instead the cycle may remove only half the amount. Another approach is to operate the pressure chamber 43 with subpressure during a predetermined time, for example 5 minutes, and then operate the pressure chamber 43 with an overpressure during a time of for example 5 minutes. The apparatus will then cycle the amount of fluid which is sucked into the pressure chamber during this time, which may be for example 120 ml or more or less.

The pump bag is indicated to have an inner volume of about 160 ml, but other volumes may be used as appropriate. For example, the pump bag inner volume may be 50 ml, 60 ml, 70 ml, 80 ml, 90 ml, 100 ml, 110 ml, 120 ml, 130 ml, 140 ml, 150 ml, 160 ml, 170 ml, 180 ml, 190 ml, 200 ml, 210 ml, 220 ml, 230 ml, 240, 250 ml or 300 ml.

Figure 11:
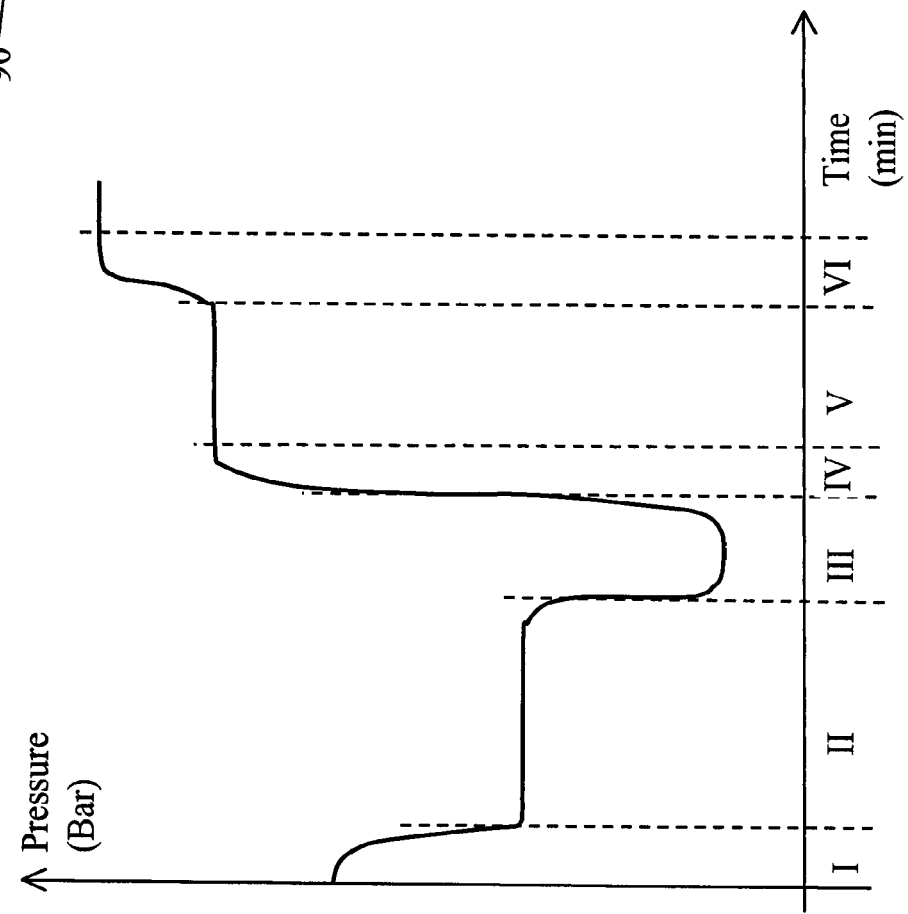
FIG. 11 is a diagram showing pressures during a cycle.

The progress of the fill of the pump bag and the emptying of the pump bag may be monitored by the air pressure meter 47, see FIG. 11. During normal operation during a suction step, the pump 45 is started in a revers direction and sucks out air from the pressure chamber 43 with a rate which is determined by the air flow capacity of the pump, see time phase I in FIG. 11. Thus, the pressure inside the pressure chamber decreases with a specific exponential decrease rate according to a characteristic exponential curve.

When there is a sufficient negative pressure in the pressure chamber 43, fluid starts to flow into the pump bag 41, whereby the pump bag inside the pressure chamber increases in volume. During this fluid inflow time, the negative pressure in the pressure chamber 43 is substantially constant, for example about −0.075 Bar, as indicated during time phase II in FIG. 11. When the pump bag 41 is full with fluid, the negative pressure again starts to lower until the lowest possible pressure of about −0.2 Bar is obtained, see time phase III in FIG. 11.

During the fill period, the opposite actions take place. First the pump 45 is driven in the forward direction and pumps air into the pressure chamber 43 according to a characteristic exponential curve, see time phase IV in FIG. 11. When the positive pressure is sufficiently high for expelling fluid from pump bag 41, the positive pressure in the pressure chamber is approximately constant, for example about +0.125 Bar, during an outflow time, se time phase V in FIG. 11. Finally, when all fluid has been expelled from pump bag 41, the positive pressure increases exponentially until maximum pressure of about +0.2 Bar has been obtained, see time phase VI in FIG. 11.

The glucose pump is only operated during time phases II and/or V, when there is an outflow and/or inflow.

As is evident from FIG. 11, the start pressure may be different from 0 Bar, which means ambient pressure. Such difference may depend on the height position of the apparatus in relation to the peritoneal cavity and also any positive pressure inside the peritoneal cavity, which may be present.

Such pressure curves are dependent on many factors. However, the curves can be used for indicating any malfunction. For example, if there is no portion of substantially constant pressure in the pressure curve, the inflow and outflow of the pump bag 41 may be compromised of any reason. Such reason may be that the patient line 20 is kinked or that the catheter into the patient is partly obstructed or that there is an obstruction between the cassette 25 and the pump bag 41. Thus, an alarm can be given.

The time duration of the constant flow portion may be used as an indication of the flow rate, which may be used for controlling the glucose pump, so that the glucose concentration of the fluid flowing to the peritoneal cavity never exceeds the predetermined safe value of for example 3%.

The decrease to the minimum pressure of −0.2 Bar can be used as an indication that the pump bag 41 is full and that the cycle should continue.

The increase to the maximum pressure of +0.2 Bar can be used as an indication that the pump bag 41 is empty and that the cycle should stop.

The reading of the air pressure meter 47 may be compared with the fluid pressure meter 51. If the pressure of air pressure meter 47 is above the pressure of fluid pressure meter 51 it is an indication that the pump bag is empty (and vice versa).

The reading of the air pressure meter 47 may be compared with the fluid pressure meter 51. When there is a flow into the pump bag 41, the fluid pressure meter 51 indicates at least a small subpressure, which is present in the cassette. When the flow stops because the pump bag 41 is full, the pressure in the cassette and the fluid pressure meter 51 returns to normal pressure, while the pressure inside the pressure chamber, measured by the air pressure meter 47 is still low (−0.2 Bar). This is a distinct indication that the pump bag is full. The same applies vice versa when the pump bag 41 is emptied.

If there is a stop in the patient line 22, because of a kink or of any other reason, the pressure inside the cassette measured by the fluid pressure meter 51 will be the same as the pressure inside the pressure chamber, measured by the air pressure meter 47. If this happens, an alarm is given.

The fluid pressure meter 51 is also used for monitoring that the pressure caused by glucose pump 16 will not be excessive. As soon as the pressure of fluid pressure meter 51 increases above for example 0.25 Bar and/or decreases below for example −0.25 Bar, an alarm is issued or indicated. These thresholds may be adjusted in dependence of the apparatus level in relation to the peritoneal cavity, for example by calibration of the fluid pressure meter 51 during start-up of the treatment or before start of a cycle, for example before the start of each third cycle.

Figure 2:
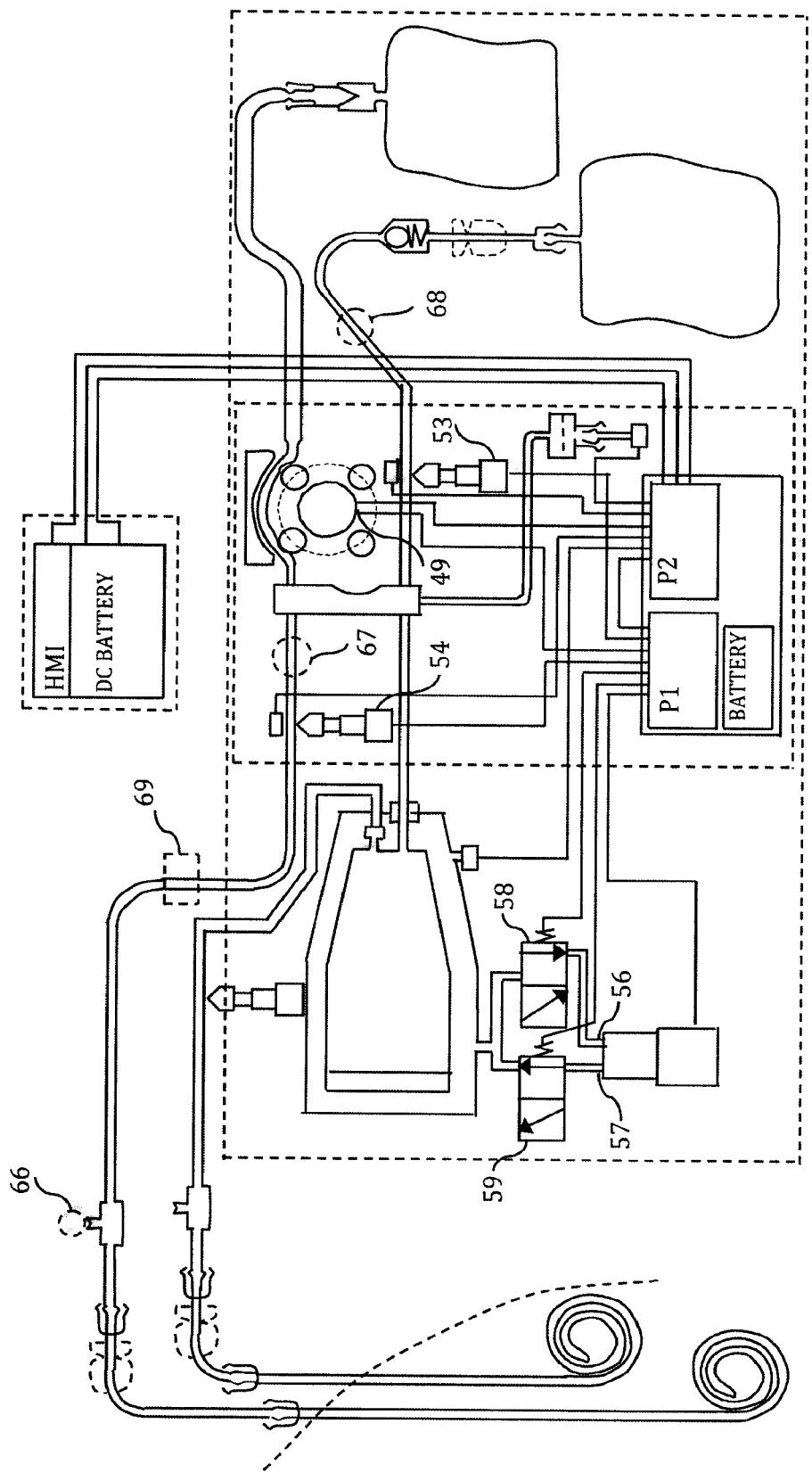
FIG. 2 is a schematic diagram of a second embodiment of the apparatus for providing and regenerating an ultrafiltration fluid to a patient.

The embodiment described above may be used when the patient has a single lumen patient line. The apparatus may be adapted to a double lumen catheter or two catheters, for example as indicated in FIG. 2. In this case, a second inlet to the pump bag 41 is connected to the other lumen or the other catheter via a second patient tube having a second patient valve. During the suction phase, the second patient valve is opened while the first patient valve is closed. Thus, fluid is sucked into the pump bag via the second patient tube. The reintroduction of the fluid into the peritoneum takes place as described above. The patient valves may be replaced by non-return valves. The operation is still intermittent.

FIG. 2 additionally shows an alternative design of the air pump. The air pump 55 has a suction port 56 and a pressure port 57 controlled by electronically operated valves 58, 59. Thus, reversion of the flow takes place by adjustment of the valves, while the electric motor and the pump always runs in the same direction and with the same speed. The electric motor may be run continuously during the cycle period and is only stopped between consecutive cycles.

The computer 60 is provided with signals from fluid pressure meter 51, air pressure meter 47, the revolution meter 49 at the glucose pump 16, which detects each step of the glucose pump 16, a drain valve switch 53 and a patient valve switch 54. These input signals are input to processor card 63, which is connected with processor card 62. The processor card 63 output control signals to air pump motor 46, air control valves 58, 59, patient valve 28, glucose pump 16 and drain valve 17 for operating these devices according to any processor program. The processor may also comprise a battery 64 for operation of the different components.

In addition, the remote control 61 is connected to processor card 63 in order to input control signals. The remote control 61 also comprises a battery 65. If the connection between remote control 61 and the apparatus is broken, the apparatus stops to operate and is put into a secure position.

The battery 64 may be a small capacity battery which is only used in emergency situations, when the battery 65 of remote control is disconnected. In this case, battery 64 has a sufficient capacity for placing the two valves 17 and 18 in a safe configuration, for example close the two valves. When the battery 65 of remote control is connected again, battery 64 is charged again. Thus, the power for operating the apparatus is taken from the battery 65 included in the remote control.

Alternatively, battery 65 is a small capacity battery, which is used only for back-up purpose, for example for keeping a clock circuit operating, while the apparatus is operated by battery 64.

One or both batteries 64, 65 may be rechargeable batteries.

Figure 3:
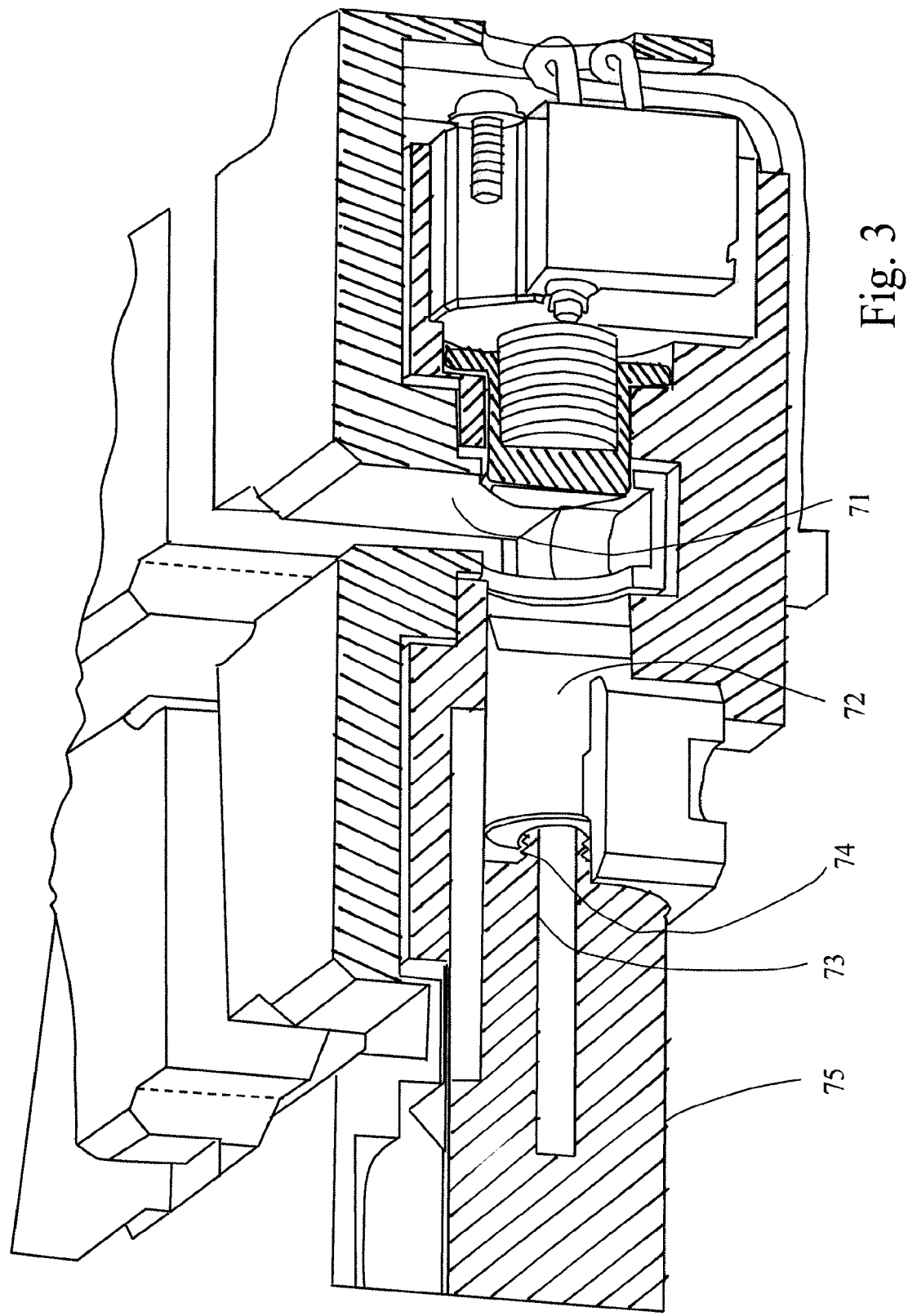
FIG. 3 is a partly cut section of a valve used in the above embodiments.
Figure 4:
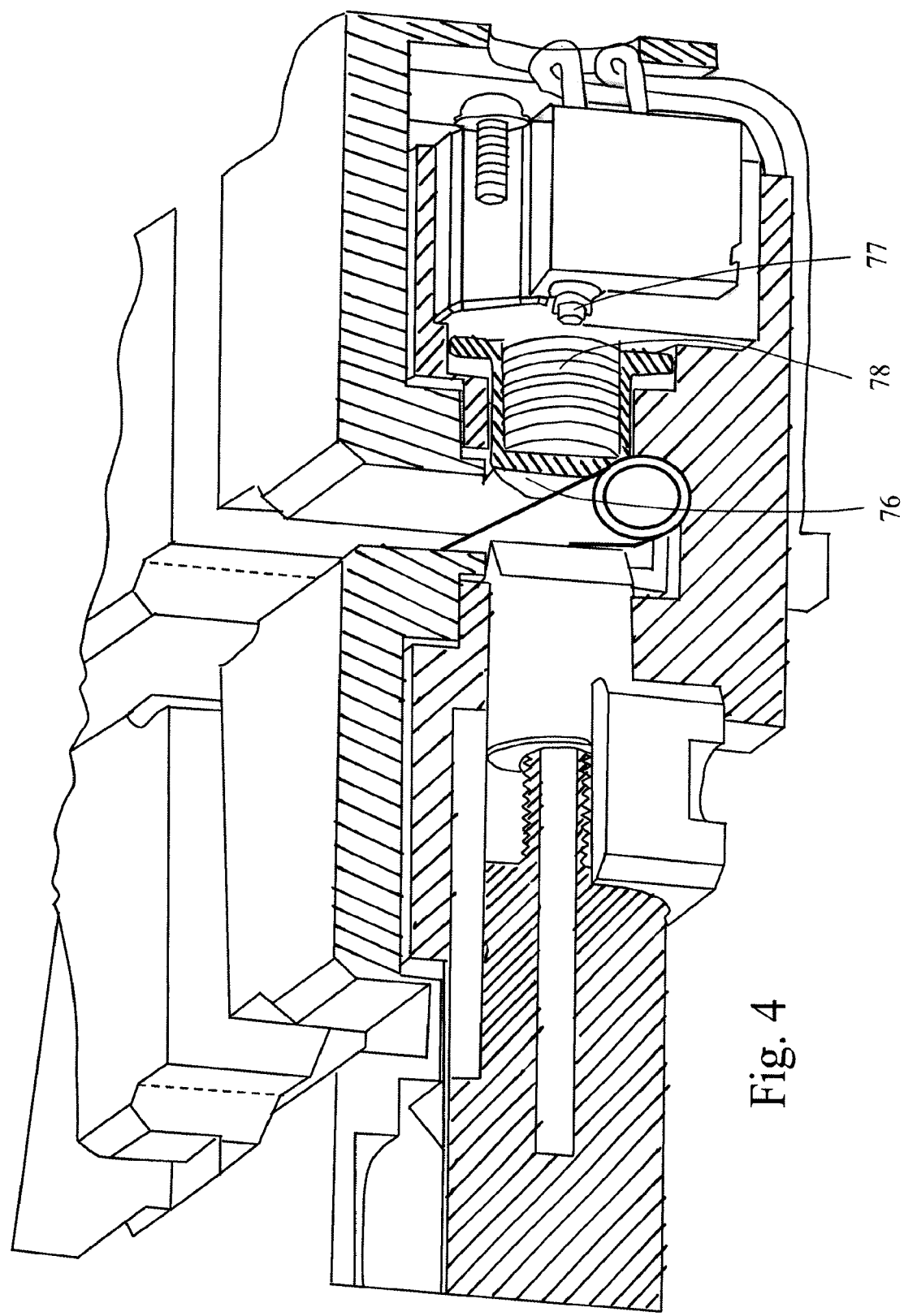
FIG. 4 is a partly cut section of the valve of FIG. 3 in an activated position.

FIG. 3 shows the patient valve or the drain valve, which are equal. FIG. 3 shows the valve in a non-activated position and FIG. 4 shows the valve in an activated position, by broken lines. The valve comprises a U-shaped groove 71 in which the corresponding tube is to be arranged, see further below. The valve further comprises a plunger 72, which is substantially cylindrical and is moveable perpendicular to the tube by means of a screw 73, nut 74 and electric motor 75. When the motor is activated, the plunger moves into engagement with the tube as shown in FIG. 4. At the opposite side of the groove, there is arranged a button 76 which protrudes slightly into the groove and is urged to the shown position by a spring 78. When the tube is pressed by the plunger as shown in FIG. 4, the button will yield and thereby activates a switch 77, connected to the processor card 63 for indicating that a sufficient valve closure pressure has been obtained.

Figure 5:
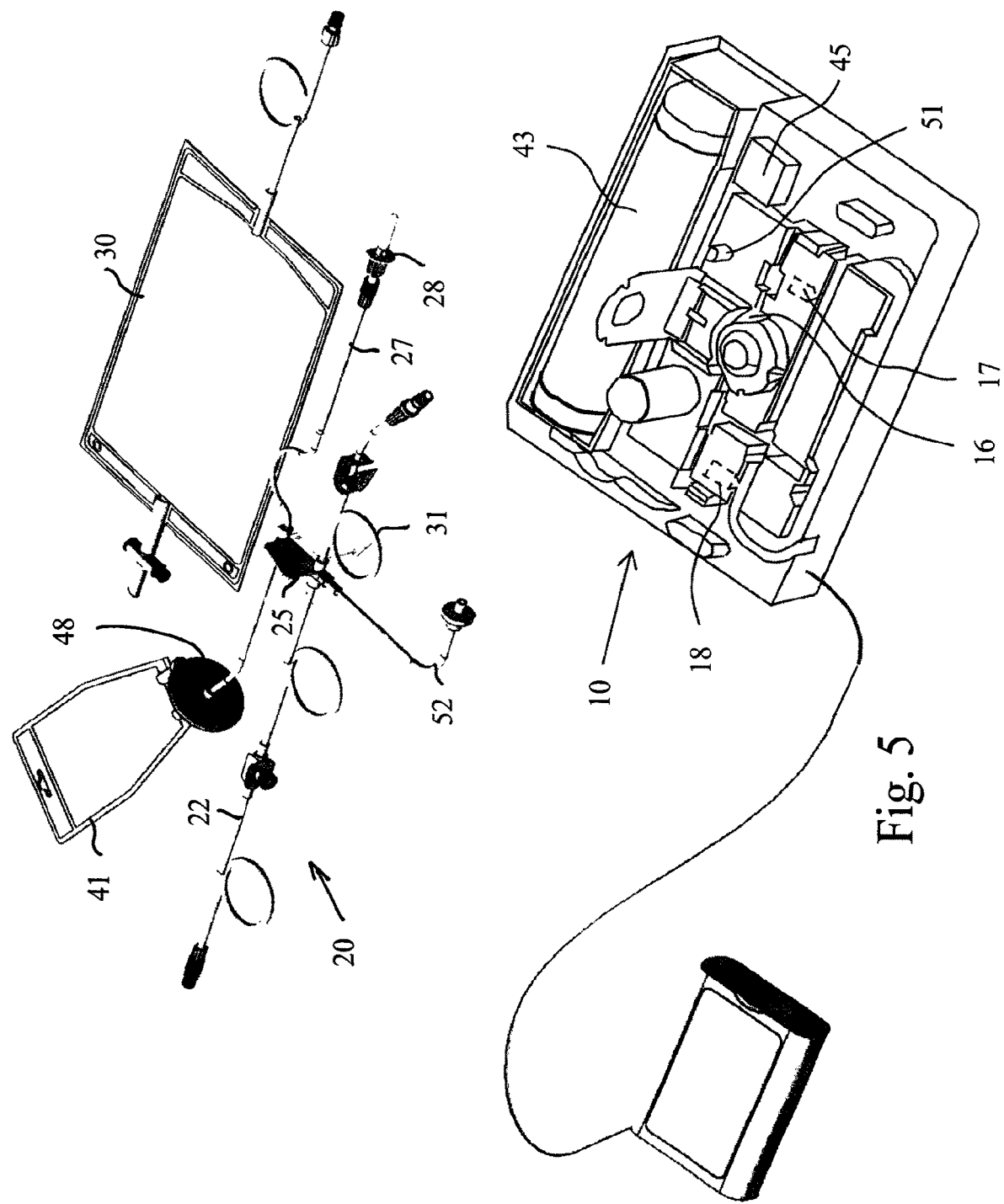
FIG. 5 is a perspective view of the tube set and apparatus according to an embodiment of the invention.

FIGS. 5 to 9 shows the complete apparatus during set-up. FIG. 5 shows the different components, namely a tube set 20 and an apparatus 10. As described with reference to FIG. 1, the tube set comprises the patient tube 22, cassette 25, fluid pressure meter tube 52, drain tube 31, pump bag 41 and glucose tube 27. The drain bag 30 is a separate component of the tube set 20 and is connected to drain bag 30 by a Luer connector. The glucose bag is also a separate component and is not shown in FIG. 5 but is connected by means of spike 28. The apparatus 10 comprises peristaltic glucose pump 16, patient valve 18 and drain valve 17, fluid pressure meter 51, pressure chamber 43 and air pump 45.

Figure 6:
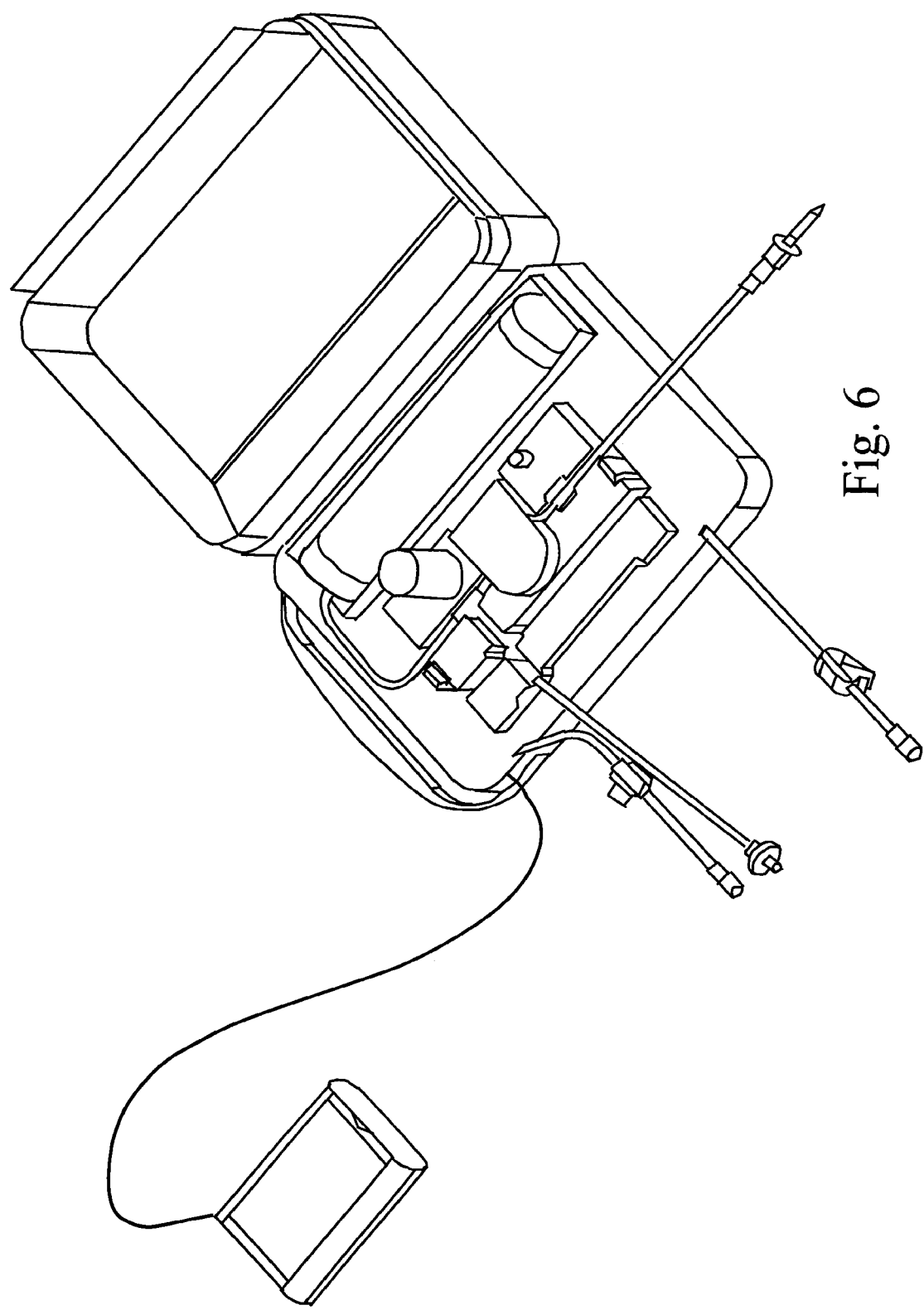
FIGS. 6 to 9 are perspective views of the embodiment according to FIG. 5 in different assembling positions.

FIG. 6 shows the tube set 20 arranged in the apparatus in grooves. The pump bag 41 comprises a circular lid 48 (see FIG. 5) provided with a sealing. The lid fits inside the open left end of cylindrical pressure chamber 43, which may be pivoted up to allow introduction of the pump bag at the left side thereof. When the cylinder is pivoted down, the structure to the left of the pressure chamber will retain the lid 48 in place. By having a lid with small dimensions, the sealing problems will be minimized.

Figure 7:
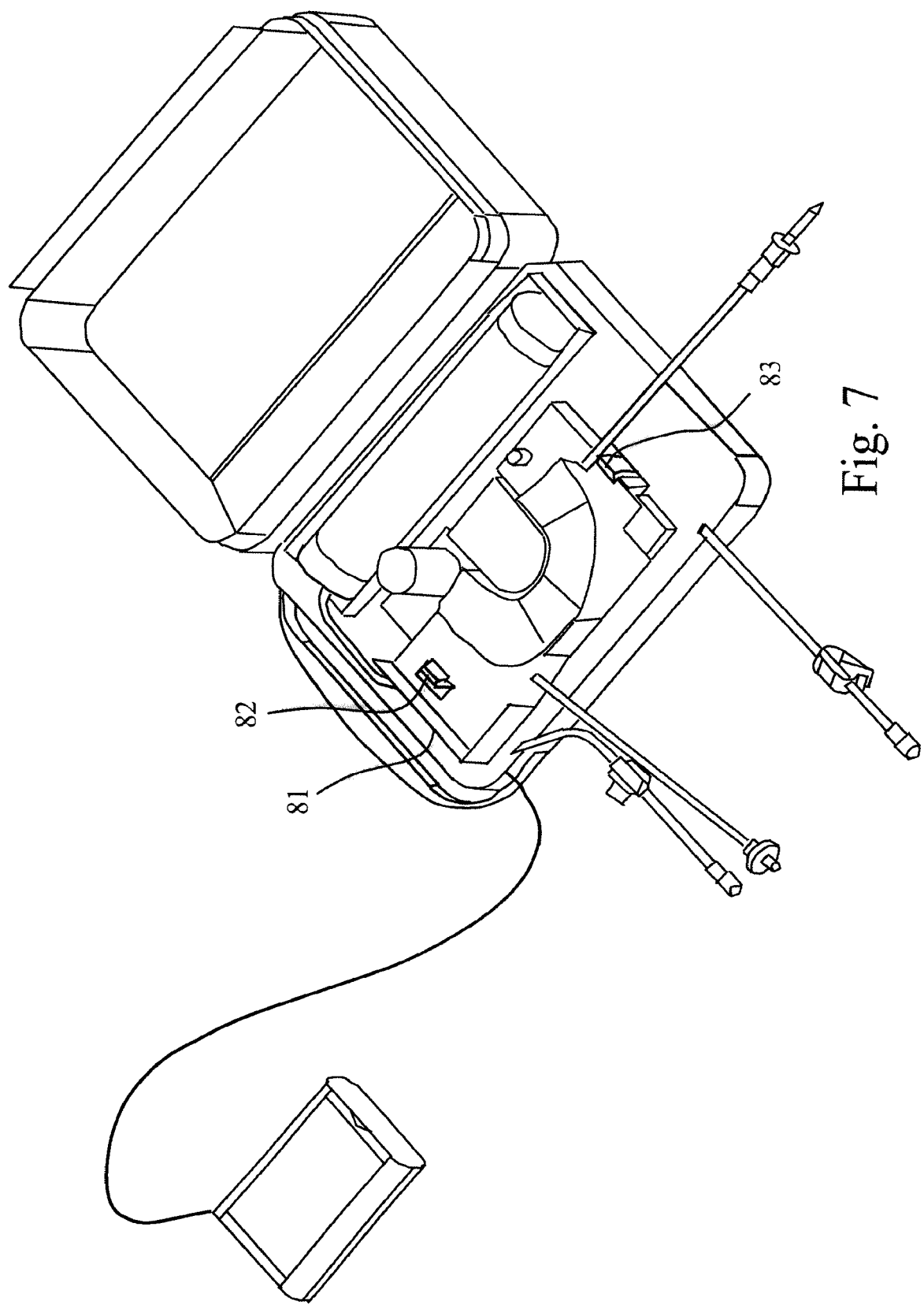
Figure 8:
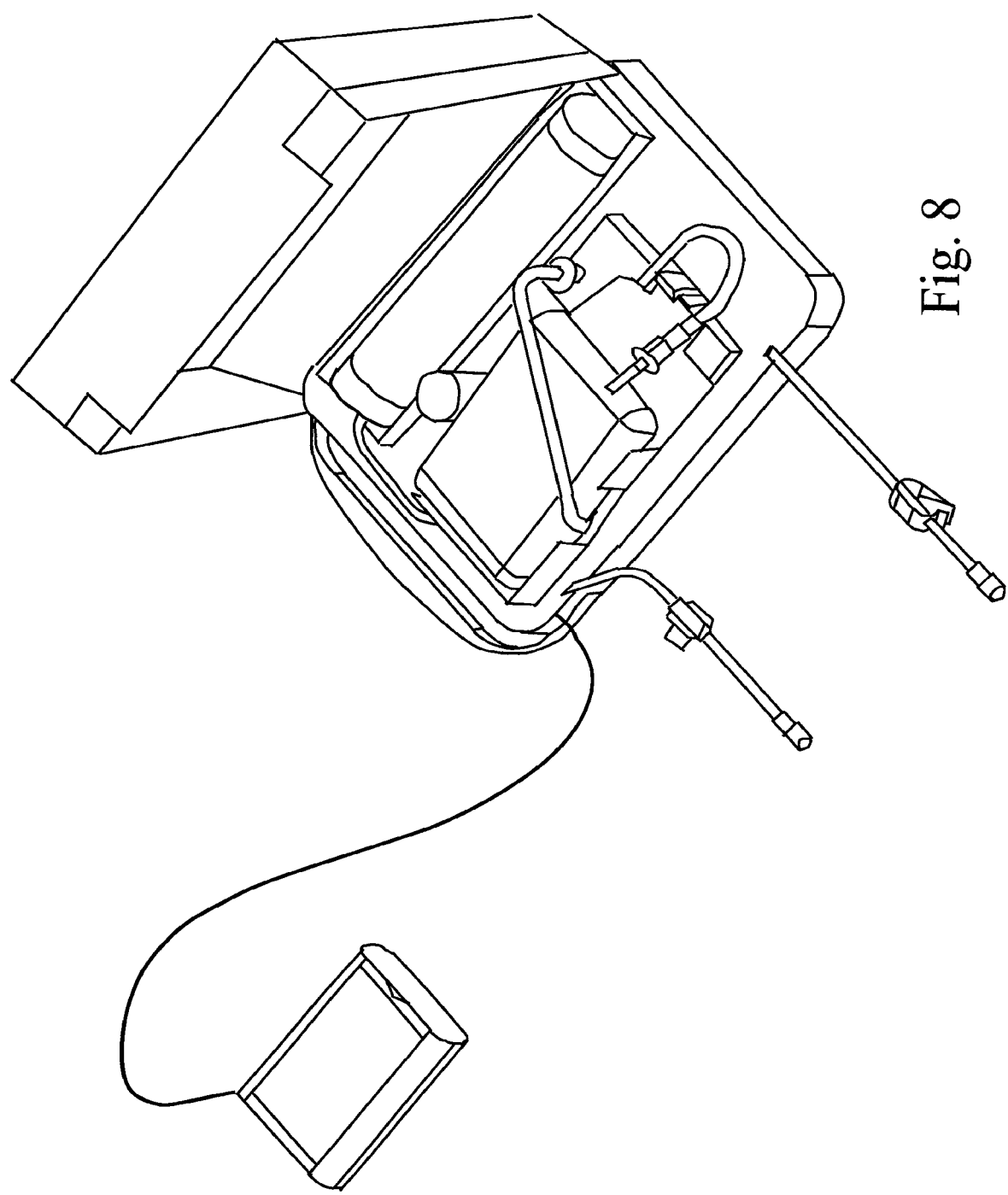
Figure 9:
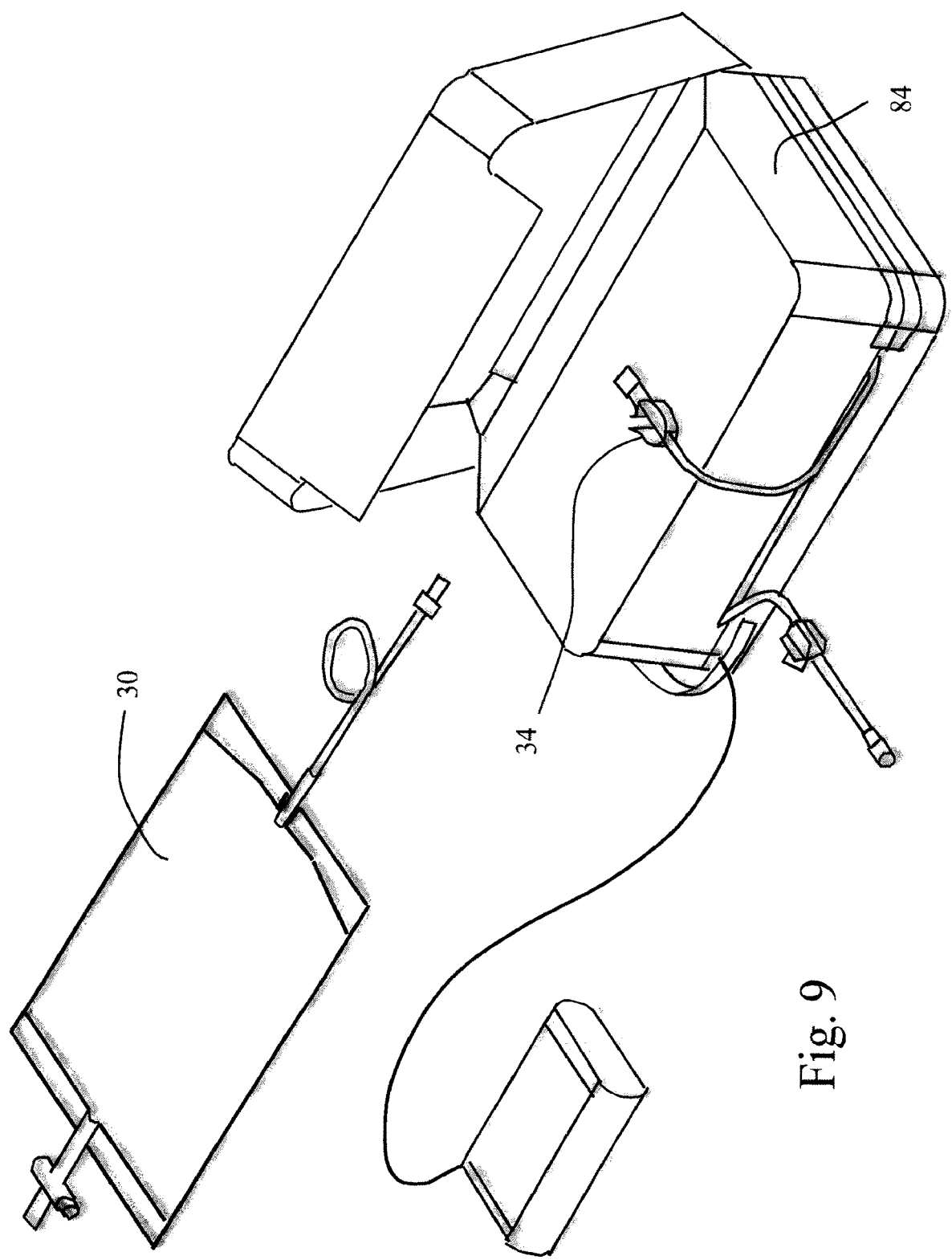

FIG. 7 shows a support structure 81, which has been arranged above the tube set 20 and is locked in place by snap locking tabs 82, 83. Inside the support structure 81, the glucose bag is arranged as shown in FIG. 8 and connected to the tube set via the spike 28. Finally a cover structure 84 is arranged above the glucose bag and the drain bag 30 is place upon the cover structure as shown in FIG. 9. The drain bag may be connected or removed as the case may be at any time by closing the tube clamp 34 and removing/attaching the Luer connector.

Figure 10:
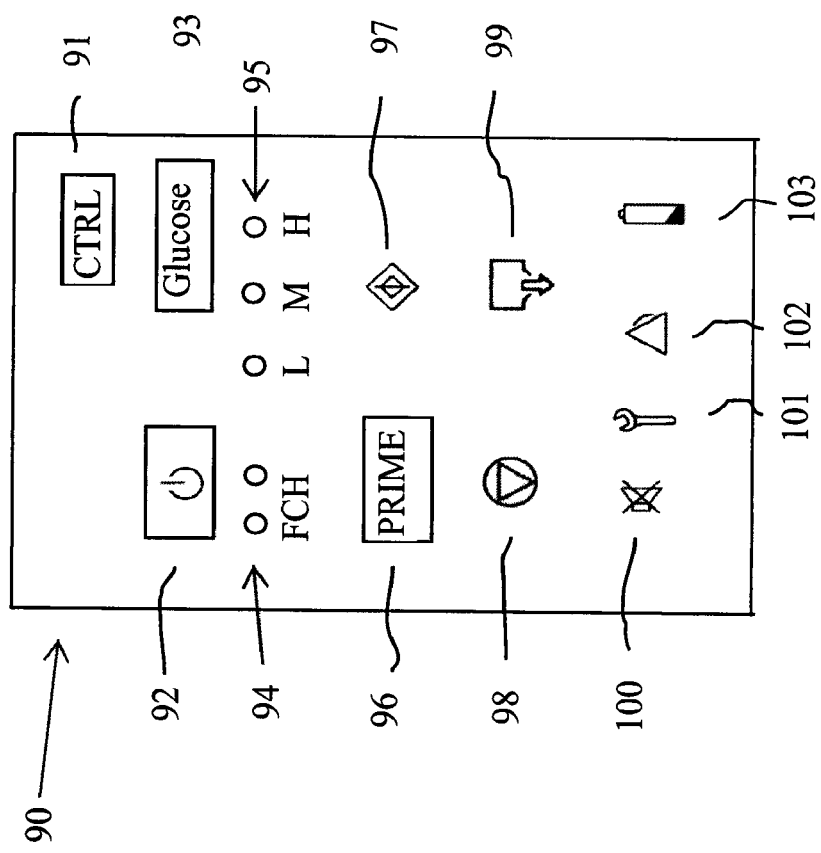
FIG. 10 is a plan view of a remote control to be used in the embodiment of FIGS. 5 to 9.

FIG. 10 shows the layout of the remote control 90. The control comprises a number of buttons and LED:s having the following functions: Up to the right, there is a Control Button 91 which is used to obtain an action. There below is an On/Off button 92 and a Glucose Button 93. Below the On/Off button, there is arranged two LED:s 94 indicating Function check 1 and 2. Below the Glucose Button, there is arranged three LED:s 95 indicating different glucose concentrations, Low, Medium and High. The concentrations can be altered only before start of the treatment. There below, there is arranged a Prime Button 96 and a Start Button 97, with corresponding LED:s. There below, there is arranged a pump button 98 and a Drain Button 99 and LED:s indicating corresponding action. In the bottom row, there is arranged a Mute Button 100 and LED:s indicating Service Alarm 101, User Alarm 102 and Low Battery indicator 103.

The patient having heart failure may also have low blood pressure, which may compromise the operation of the kidney. The kidney may require support in removal of excess water, since the urine production is smaller than normal. However, the excretion of metabolic waste products, such as urea and creatinine, may normally be sufficient.

However, because of the low urine volume, an insufficient removal of sodium may prevail. Thus, the fluid used in these embodiments may be modified by reducing the sodium concentration, which results in removal of sodium, in addition to removal of water as described above. If the removal of potassium of the kidney is too low, a lowering of the potassium concentration in the starting fluid may be appropriate, or even elimination of potassium from the fluid. However, the body is sensitive to low potassium concentration in blood, and a lowering or removal of the potassium concentration should be carefully supervised by a doctor.

The patient having heart failure may have a compromised blood pressure as indicated above. Such blood pressure may result in partial withdrawal of capillaries in the peritoneal membrane and adjacent tissue, resulting in less exchange of substances between the fluid in the peritoneal cavity and the blood. The result is less ultrafiltration. However, the continuous supply of glucose is expected to reduce any tendency for the capillaries to withdraw, since the body is not exposed to transient conditions. Thus, the gentle and continuous replenishment of glucose is expected to be of great importance for sensitive patients.

The peritoneal membrane is sensitive to excessive exposure to glucose, which may result in peritonitis or other problems. A gentle exposure of the peritoneal membrane to glucose may counteract such problems. Accordingly, the initial installation of fluid into the peritoneal cavity may take place with a low concentration of glucose, or even zero glucose. Then, the concentration of glucose is increased slowly during the next 30 minutes.

Due to the fact that a replenishment of glucose is made intermittently with short intervals, a low concentration of glucose may be used and still a desired ultrafiltration may be achieved. This is advantageous for avoiding pain and peritonitis as well for maintaining the ultrafiltration function of the peritoneal membrane.

If the patient during the treatment is exposed to hypotension or other problems, resulting in withdrawal of capillaries in the peritoneal membrane, this is manifested as a lowering of the ultrafiltration and a lowering of glucose absorption. On the other hand, continuous exposure to glucose, lactate and low pH may result in morphologic damage that may have a causative role in changes in peritoneal function.

Glucose levels in the fluid may be monitored by the glucose sensor. If glucose levels becomes too low or too high an alarm to the patient and/or supervising persons may result. Then, the treatment may be interrupted or other actions undertaken to obtain adequate glucose levels.

A glucose sensor 66 may be arranged in the sample port 23, as shown in FIG. 2. Alternatively or additionally, a glucose sensor 67 may be arranged in the tube set, for example adjacent the cassette 25. Since a glucose sensor may be sensitive to constant exposure to glucose, a glucose sensor 68 may advantageously be arranged in the drain tube 31 after the drain valve 17. When the glucose concentration should be measured, the drain valve 17 is opened for a short time period and the measurement is performed. In this way, the glucose sensor 68 is exposed for glucose only during short intervals. Several glucoses sensors may be used.

The flow in the patient tube 22 may be measured by a flow meter 69, as shown in FIG. 2.

The treatment is continued for a long time, at least six hours. In an embodiment, the treatment is performed daily during 16 hours. In another embodiment, the treatment is nocturnal. Such treatment may last for 8 hours or more. Before the treatment, a new fluid is introduced. After the treatment, all fluid may be drained. The difference in installed and removed fluid may be measured in order to calculate obtained ultrafiltration. A conventional PD solution may be used. The fluid volume of the administered glucose should be accounted for as well.

The glucose bag may comprise glucose at a concentration of 10%, 20%, 40% or 50% and may have a volume of about 0.5 liter, 0.25 liter, 0.125 liter or 0.1 liter. The volume of fluid entered into the peritoneal cavity may be between 1 and 3 liters, for example 1.5 liter. The fluid may comprise ions of sodium 132 mM (125-150) (mmol/liter), potassium 2 mM (0-4.5), calcium 2.5 mM (0-2.5), magnesium 0.5 mM (0.25-1.5), chloride 95 mM (90-120) and lactate 40 mM (30-60) and should be isotonic or hypertonic. Lactate may be (partly) replaced by acetate or bicarbonate.

The glucose may be provided as a dry powder, which is diluted by the apparatus. During the initial priming, in an initial step, the glucose pump 16 is operated in a reverse direction to pump fluid into the glucose bag 26 comprising dry powder glucose. The glucose bag may be squeezed several times in order to dissolve the powder. Another alternative is to provide a glucose bag having several compartments, one of which comprises dry powder glucose.

If sodium ions should be removed, the sodium ion concentration may be lowered to 110 mM or lower. The potassium concentration may be lowered or removed. The calcium concentration may be lowered or removed.

The glucose bag may comprise some sodium or no sodium, in order to influence upon the sodium balance.

The osmotic agent mentioned above is glucose, which has been shown to be working well for ultrafiltration of peritoneal dialysis patients. However, other osmotic agents may be used such as Icodextrin, which is a glucose polymer.

An alternative manner of filling the peritoneal cavity from the start would be according to the following method. Firstly, a start fluid bag comprising a predetermined start fill volume of fluid, for example 1.66 liter of fluid is connected to the sample port 23 or to a dedicated connection port in the form of a Luer connector by means of a tube by an aseptic technique. The start fluid bag is arranged at a height of about 50 cm above the patient connector 4. Patient line clamp 5 is initially closed and patient valve 18 is also closed. There is a lid arranged on patient line connector so no fluid can flow from the start fluid bag until the lid is removed. When the lid is removed, a small amount of start fluid is allowed to drain from the connector (to rinse the connector) and then the connector 21 is connected to patient connector 4 and patient clamp 5 is opened. Now, fluid starts to fill the peritoneal cavity, which may take some time, such as about 30 minutes. As soon as the connection is made, the patient presses a priming button, whereby the above priming sequence starts as described above. Fluid is taken from the start fluid bag and at the same time the peritoneal cavity is filled. When the priming step is ready, 0.16 liter have been removed by the apparatus to the drain bag and 1.5 liter has been introduced into the peritoneal cavity. Now, the apparatus automatically starts a cycle (if further glucose should be added to the peritoneal start fluid as discussed above), comprising generating a suction pressure in the pump bag 41, followed by a positive pressure. During both these steps the glucose pump may be operated. The filling of the peritoneal cavity does not need to be finalized. The procedure of the apparatus may be continued independently of the filling from the start fluid bag.

When the start fluid bag is empty, the desired fluid volume of 1.5 liter has been installed in the peritoneal cavity.

Another volume of fluid can be installed according to the prescription of the physician, such as 1.0 liter, 1.2 liter, 1.7 liter or 2.0 liter. The start fluid bag is now disconnected (or may be left connected but occluded from inflow by a clamp) and may be stored for a final emptying of the peritoneal cavity.

In this manner, time is saved when the apparatus is started.

The maximum and minimum pressures have been indicated to be +0.2 Bar respectively −0.2 Bar. This corresponds to a waterpillar of roughly about 200 cm. However, normal inflow and outflow flow rates may be obtained by a waterpillar of between 50 cm and 100 cm, corresponding to between 0.05 Bar and 0.1 Bar. However, the flow of fluid out of and into the peritoneal cavity may be controlled by the flow rate of the air pump. If the flow rate of airpump is adjusted to provide a fluid flow of for example 32 ml/min, the corresponding pressures will automatically be obtained. Alternatively, the fluid flow rate may be measured and the airpump may be operated in order to obtain the desired fluid flow rate.

In the claims, the term "comprises/comprising" does not exclude the presence of other elements or steps. Furthermore, although individually listed, a plurality of means, elements or method steps may be implemented by e.g. a single unit. Additionally, although individual features may be included in different claims or embodiments, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality. Reference signs in the claims are provided merely as a clarifying example and shall not be construed as limiting the scope of the claims in any way.

Although the present invention has been described above with reference to specific embodiment and experiments, it is not intended to be limited to the specific form set forth herein. Rather, the invention is limited only by the accompanying claims and, other embodiments than those specified above are equally possible within the scope of these appended claims.

The invention claimed is:

1. An apparatus for conducting ultrafiltration using a peritoneal membrane of a patient, the apparatus comprising:
 a patient tube comprising a connector for connection to a patient line for access to a peritoneal fluid installed in a peritoneal cavity of the patient;
 an intermittent bag connected to said patient tube;
 a flow pump for removal of a portion of said peritoneal fluid via said patient tube in an outflow of fluid from the peritoneal cavity into the intermittent bag and for return of contents of said intermittent bag in an inflow of fluid from the intermittent bag to the peritoneal cavity;
 a glucose bag, comprising concentrated glucose solution;
 a glucose tube connecting said glucose bag to said patient tube; and
 a glucose pump arranged in said glucose tube for addition of concentrated glucose solution from said glucose bag into said outflow of fluid, such that the concentrated glucose solution is diluted and included in the inflow of fluid to the peritoneal cavity to intermittently replenish the peritoneal fluid installed in the peritoneal cavity with glucose that causes the ultrafiltration to be conducted.

2. The apparatus according to claim 1, wherein said outflow of fluid takes place in a first flow path and said inflow of fluid takes place in a second flow path, which is the same as said first flow path.

3. The apparatus according claim 1, wherein said glucose pump is arranged to dilute the concentrated glucose solution from said glucose bag from a concentration of one of: 10%, 15%, 20%, 25%, 35%, 40% or 50% to a predetermined diluted concentration before inclusion in the inflow of fluid from the intermittent bag to the peritoneal cavity.

4. The apparatus according to claim 1, wherein said glucose pump is arranged to dilute the concentrated glucose solution to a final concentration of less than one of: 2%, 2.5%, 3%, 3.5%, 4%, 4.5%, 5%, 6%, 7%, 8%, 9% or 10% before inclusion in the inflow of fluid from the intermittent bag to the peritoneal cavity.

5. The apparatus according to claim 1, wherein said flow pump comprises:
 a pressure chamber having a constant volume, wherein said intermittent bag is a pump bag arranged inside said pressure chamber, and
 an air pump for generating a negative pressure inside said pressure chamber for the removal of fluid in said outflow from said peritoneal cavity into said pump bag, and for generating a positive pressure for the return of fluid in said inflow from said pump bag to the peritoneal cavity.

6. The apparatus according to claim 5, further comprising an air pressure meter arranged to measure the air pressure in said pressure chamber and a fluid pressure meter arranged to measure a fluid pressure in said patient tube, wherein an evaluation device is arranged to compare the air pressure in said pressure chamber, during the inflow and the outflow, with the fluid pressure in said patient tube, for indicating a flow when the pressure difference is smaller than a third predetermined value.

7. A method for conducting ultrafiltration using a peritoneal membrane of a patient, comprising:
 removing a portion of peritoneal fluid, which is installed in a peritoneal cavity of a patient, from the peritoneal cavity to an intermittent bag in an outflow of fluid from the peritoneal cavity;
 adding concentrated glucose solution to said outflow of fluid by a glucose pump from a glucose bag containing concentrated glucose solution for dilution of said concentrated glucose solution in said portion of peritoneal fluid in said outflow of fluid; and
 returning said portion of peritoneal fluid including said diluted glucose solution in an inflow of fluid from the intermittent bag to the peritoneal cavity to intermittently replenish said peritoneal fluid installed in the peritoneal cavity with glucose that causes the ultrafiltration to be conducted.

8. The method according to claim 7, further comprising: repeating said removing and said returning of said portion of peritoneal fluid and said adding of concentrated glucose solution intermittently with a period of not greater than 60 minutes.

9. The method according to claim 7, further comprising providing, within said glucose bag, the concentrated glucose solution at a concentration of one of: 10%, 15%, 20%, 25%, 35%, 40% or 50%.

10. The method according to claim 7, wherein the concentrated glucose solution is diluted to a final concentration of less than one of: 2%, 2.5%, 3%, 3.5%, 4%, 4.5%, 5%, 6%, 7%, 8%, 9% or 10% before the returning to the peritoneal cavity.

11. The method according to claim 7, wherein said flow pump comprises a pressure chamber having a constant volume, wherein said intermittent bag is a pump bag arranged inside said pressure chamber,
said flow pump generating a negative pressure inside said pressure chamber for the removal of fluid in said outflow from said peritoneal cavity into said pump bag, and
said flow pump generating a positive pressure for the return of fluid in said inflow from said pump bag to the peritoneal cavity.

12. The method according to claim 11, wherein an air pressure meter in said pressure chamber is arranged to indicate when the pump bag is filled by:
measuring a decrease of pressure in said pressure chamber compared to an outflow pressure;
measuring a constant pressure in said pressure chamber during said outflow; and
measuring a decrease of pressure in said pressure chamber to a minimum pressure after said outflow;
wherein an evaluation device is arranged to indicate an error if a time period of the measured constant pressure in said pressure chamber is less than a predetermined time period.

13. The method according to claim 11, wherein an air pressure meter in said pressure chamber is arranged to indicate when the pump bag is empty by:
measuring an increase of pressure in said pressure chamber compared to an inflow pressure;
measuring a constant pressure in said pressure chamber during said inflow; and
measuring an increase of pressure in said pressure chamber to a maximum pressure after said inflow;
wherein an evaluation device is arranged to indicate an error if a time period of the measured constant pressure in said pressure chamber is less than a predetermined time period.

14. The method according to claim 7, wherein said outflow of fluid takes place in a first flow path and said inflow of fluid takes place in a second flow path, which is the same as said first flow path.

15. The method according to claim 7, wherein said outflow of fluid is followed without delay by said inflow of fluid, which is followed without delay by another outflow of fluid and so on.

* * * * *